United States Patent [19]
Gurley et al.

[11] Patent Number: 5,196,329
[45] Date of Patent: Mar. 23, 1993

[54] 780 T-DNA GENE TRANSCRIPTION ACTIVATOR

[75] Inventors: William B. Gurley, Gainesville, Fla.; Wesley B. Bruce, Fremont, Calif.

[73] Assignees: Lubrizol Genetics Inc., Wickliffe, Ohio; The University of Florida, Gainesville, Fla.

[21] Appl. No.: 587,517

[22] Filed: Sep. 24, 1990

Related U.S. Application Data

[63] Continuation of Ser. No. 135,147, Dec. 18, 1987, abandoned.

[51] Int. Cl.$^5$ .................. C12N 15/00; C07H 15/12
[52] U.S. Cl. ...................... 435/172.3; 435/320.1; 536/24.1; 935/35; 935/36; 935/67
[58] Field of Search .............. 435/172.3, 320.1; 536/27; 935/35, 36, 67

[56] References Cited

PUBLICATIONS

McKnight et al. 1982, Science 217:316-324.
Gurley et al. 1987, pp. 279-288 In: Plant Gene Syst. Their Biol. (UCLA Symp. Mol. Cell. Biol., New Ser., 62).
Bruce et al. 1988, Proc. Natl. Acad. Sci. USA 85:4310-4314.
Bruce et al. 1987, Mol. Cell Biol. 7:59-67.
Kaluza et al. 1985, FEB Letters 188(1):37-42.
DeGreve, H. et al. (1982) J. Mol. Appl. Genet. 1:499.
Bevan, M. et al. (1983) Nucl. Acids Res. 11:369.
Depicker, A. et al. (1982) J. Mol. Appl. Genet. 1:561.
Koncz, C. et al. (1983) EMBO J. 2:1597-1603.
Shaw, C. et al. (1984) Nucl. Acids Res. 12:7831.
An, G. et al. (1986) Mol. Gen. Genet. 203:245.
Ellis, J. et al. (1987) EMBO J. 6:11.
DiRita, V. and Gelvin, S. (1987) Mol. Gen. Genet. 207:233.
Barker, R. et al. (1983) Plant Mol. Biol. 2:335.
Gurley, W. et al. (1986) Mol. Cell Biol. 6:559.

*Primary Examiner*—David T. Fox
*Attorney, Agent, or Firm*—Greenlee and Winner

[57] ABSTRACT

A DNA sequence element, which activates or enhances expression of genes in plants has been identified and characterized. In particular, DNA segments isolated from the upstream region of the T-DNA 780 gene are capable of activating or increasing transcription levels of plant-expressible genes in recombinant DNA-containing plant tissue. The 780 gene transcription activator is useful in general for increasing the level of expression of a gene in a plant. In particular, such activators are useful in the construction of plant-expression complexes which contain a plant-expressible gene placed under the regulatory control of the activator. Such expression complexes can be introduced into plant tissue where the inserted gene in expressed.

34 Claims, 2 Drawing Sheets

FIG. 1A pTi15955

780 T-DNA GENE TRANSCRIPTION ACTIVATOR

This application is a continuation of application Ser. No. 135,147, filed Dec. 18, 1987, now abandoned.

FIELD OF THE INVENTION

This invention is in the field of plant molecular biology and relates to plant genetic engineering by recombinant DNA technology. This invention specifically relates to the identification, characterization, and utilization of DNA segments which are capable of activating or increasing the transcription of a plant-expressible gene in recombinant DNA-containing plant tissue.

BACKGROUND OF THE INVENTION

In eukaryotic genes there is a growing understanding of the DNA sequence elements which direct the initiation of transcription and which regulate or modulate gene expression. The following discussion applies to genes which are transcribed by RNA polymerase II. There are sequence elements which direct the initiation of mRNA synthesis, those which control transcription in response to environmental stimuli, and those which determine the overall level of transcription.

Promoters are the portions of DNA sequence, at the beginnings of genes, which contain the signals for RNA polymerase to begin transcription of mRNA which in turn is used as a template for protein synthesis. Eukaryotic promoters are complex, and are comprised of components which include a TATA box consensus sequence in the vicinity of position −30, and often a CAAT box consensus sequence at about −75 bp 5' relative to the transcription start site, which is defined as +1 (R. Breathnach and P. Chambon (1981), Ann. Rev. Biochem. 50:349; J. Messing et al. (1983), in *Genetic Engineering of Plants*, eds. T. Kosuge, C. Meredith, and A. Hollaender, p. 211). In plants there may be substituted for the CAAT box a consensus sequence which Messing et al. (1983) have termed the AGGA box, positioned a similar distance from the cap site. Other promoter associated sequences in the 5'-untranscribed region are known which modulate or regulate the expression of downstream genes. There are sequences which respond to environmental stimuli, such as illumination or nutrient availability or adverse conditions including heat shock, anaerobiosis, or the presence of heavy metals. There are also signals which control gene expression during development, or in a tissue-specific fashion. Other sequences serve to elevate the overall level of expression of the downstream genes; such sequences have been termed "enhancers" in animal systems. In yeast, similar stimulatory sequences are known called "upstream activating sequences", which often also appear to carry regulatory information. Promoters are usually positioned 5' to, or upstream of, the start of the coding region of the corresponding gene, and the DNA tract containing all the ancillary elements affecting regulation or absolute levels of transcription may be comprised of less than 100 bp or as much as 1000 bp.

As defined by G. Khoury and P. Gruss (1983), Cell 33:313, an enhancer is one of a set of eukaryotic promoter-associated elements that appears to increase transcriptional efficiency in a manner relatively independent of position and orientation with respect to the nearby gene. The prototype enhancer is the 72 bp repeat of SV40. It is located more than 100 bp upstream from the transcription start site, and has a consensus core sequence of

```
        TTT
    GTGGAAAG.
```

As a rule the animal or animal virus enhancers can function over a distance as much as 1 kb 5', in either orientation, and can act either 5' or 3' to the gene. The sequence motif is generally reiterated several times. In animal systems enhancers have been associated with tissue-specific regulation of expression.

Homology to the SV40 animal enhancer consensus core sequence has been noted in the nontranscribed regions of plant genes. In the 5'-flanking region of the pea legumin, the sequence 5'-CCACCTCC-3', which is about 80% homologous to the complement of the SV40 animal sequence, appears at about −180 relative to the start of transcription (G. Lycett et al. (1984) Nucleic Acids Res. 12:4493). Similar sequence motifs have been noted in the 5'-regulatory regions of the light-regulated genes: chalcone synthase (H. Kaulen et al. (1986) EMBO J. 5:1) and several rbcS genes including those of tobacco, soybean and pea (R. Fluhr et al. (1986) Science 232:1106).

SV40 enhancer-homologous sequences have also been identified in the 5'-flanking regions of the maize Adh1 and Adh2 genes. In both cases the sequence of note is 5'-CACCTCC-3', and appears at about −170 in Adh2 and at about −200 in Adh1 (E. Dennis et al. (1985) Nucleic Acids Res. 13:727; D. Llewellyn et al. (1985) in *Molecular Form and Function in the Plant Genome*, eds. van Vloten-Doting, DeGroot, and T. Hall, New York, Plenum Press). A functional role for these SV40 homologous plant sequences as enhancers, however, has not been demonstrated.

Upstream sequence motifs, termed heat shock elements (HSEs), have been found to direct the induction of the heat shock genes in the response to the stress of elevated temperature in organisms as diverse as bacteria, yeast, man and plants. In Drosophila the minimal consensus sequence for the motif is 5'—C_GAA_TT-C_G_-3' (H. Pelham (1985) Trends Genet., January, pp. 31-35). The HSEs of Drosophila also exhibit some properties of enhancer elements (M. Bienz and H. Pelham (1986) Cell 45:753). W. Gurley et al. (1986) Mol. Cell. Biol. 6:559, have found sequence elements with partial homology to the Drosophila HSE consensus sequence at the 5'-end of the soybean Gmhsp17.5-E gene. A study of heat shock expression of this gene in transformed sunflower tumor tissue revealed that sequence information between −95 and the cap site was sufficient to direct thermoinducible transcription, but that sequences further upstream (between −95 and −1175) dramatically increased both induced and basal levels of transcription suggestive of enhancer activity.

Enhancer-like activities have also been associated with plant regulatory sequences that are believed to be involved in the control of tissue specific expression and expression in response to light (M. Timko et al. (1985) Nature 318: 579; H. Kaulen et al. (1986) EMBO J. 5:1; J. Simpson et al. (1985) EMBO J. 4:2723; J. Simpson et al. (1986) Nature 323:551; R. Fluhr et al. (1986) Science 232:1106). Although, in some cases sequences homologous to the SV40 enhancer or the Ty yeast enhancer and repeated sequence elements were noted in the upstream regions displaying enhancer activity, these motifs have not been correlated with the enhancer activity.

The presence of enhancer-like sequences 5' to certain genes which are highly expressed in plants has been postulated. One such report (J. Odell et al. (1985), Nature 313:810) described the stretch of 5'-nontranscribed region of the 35S gene of Cauliflower Mosaic Virus (CaMV) which is necessary for increasing the expression of a reporter gene. Analysis of the sequence in the −105 to −46 region revealed a CAAT box-like sequence, inverted repeats, and a sequence resembling the SV40 core consensus sequence for enhancers. Ow et al. (1987) Proc. Natl. Acad. Sci. USA 84:4870-4873 report that the CaMV upstream region between −168 and −89 functions in transcriptional activation of the 35S RNA gene as well as of certain heterologous plant-expressible genes. The −148/−89 upstream fragment is reported to function in either orientation 5' of reporter genes, but not when positioned 3' to the gene. Multiple duplication of portions of the CaMV upstream region (−148/−89 fragment or the −343/−90 fragment) yielded significantly higher levels of expression than that induced by a single copy of the region (D. Ow et al. (1987); R. Kay et al. (1987) Science 236;1299). It is known that although the host range of the CaMV is limited to members of the family Cruciferae, the entire 35S promoter does function in tobacco (J. Odell et al. (1985) supra; M. Bevan et al. (1985) EMBO J. 4:1921).

The upstream activating sequences (UASs) of yeast have somewhat different properties than those of animal enhancer sequence elements. Like the animal enhancers the yeast UASs generally function when inserted in either orientation, but they do not appear able to activate transcription when placed 3' to the transcription start site (L. Guarente and E. Hoar (1984) Proc. Natl. Acad. Sci. USA 81:7860; K. Struhl (1984) Proc. Natl. Acad. Sci USA 81:7865). Sequences of the activating regions of some yeast promoter elements are known, and in at least two cases, homology to the SV40 enhancer consensus core sequence was reported (B. Errede et al. (1985)Proc. Natl. Acad. Sci. USA 82:5423; G. Roeder et al. (1985) Proc. Natl. Acad. Sci. USA 82:5428). Also associated with these sequences is information allowing the cell to respond to mating type or to stimuli such as nutritional status, depending on the particular UAS.

The tumor-inducing (Ti) plasmids carried by strains of Agrobacterium contain T-DNA regions that are transferred to and integrated into plant genomes. A number of genes encoded on T-DNA are expressed in plants, including for example, those genes responsible for production of opines in T-DNA containing plant tumors. The ocs gene encoding octopine synthase is carried within the T-DNA of octopine-type Ti plasmids such as pTiAch5 and pTi15955. The gene for nopaline synthase (nos) resides within the T-DNA of nopaline-type Ti plasmids, such as pTiC58 and pTiT37. Expression of ocs and nos genes in transformed plant tissue is constitutive and is apparently not tissue specific (L. Otten et al. (1981) Mol. Gen. Genet. 183:209). It has been proposed by W. Bruce and W. Gurley (1987) Mol. Cell. Biol. 7:59 that T-DNA sequences which regulate gene expression in transformed plants would possess maximum conservation of function in plants because the host range of Agrobacterium is very broad (M. DeCleene and J. DeLey (1976) Bot. Rev. 42:89; G. Hooykaas-van Slogteren, et al. (1984) Nature 311:763). The regulatory regions of the plant-expressible genes of T-DNA are of interest as model systems for studying the mechanism of constitutive gene expression in plants.

The upstream regions of both the nos and ocs genes have been subjected to detailed analysis. Both ocs and nos and the 5'-flanking regions of these genes have been sequenced (H. DeGreve et al. (1982) J. Mol. Appl. Genet. 1:499; M. Bevan et al. (1983) Nucleic Acids Res. 11:369, A. Depicker et al. (1982) J. Mol. Appl. Genet. 1:561).

There are conflicting data in the literature regarding the extent of 5'-sequence required for maximal expression of the nos gene. C. Koncz et al. (1983) EMBO J. 2:1597-1603 reported that all signals required for maximal expression of the nos gene were within the 261 bp of sequence preceding the transcriptional start site. In contrast, C. Shaw et al (1984) Nucleic Acids Res. 12:7831, reported that sequences farther upstream than −88 were not essential for expression in a Kalanchoe leaf-and-stem test system. More recently, G. An et al. (1986) Mol. Gen. Genet. 203:245 reported that regions of upstream DNA including the TATA box (−26 to −19), perhaps the CCAAT box (−78 to −70), and a sequence between −130 and −101 are required for efficient transcription of nos. The presence of direct sequence repeats (−171 to −161 and −137 to −127) and indirect repeats (−148 to −141 and −114 to −106) in the nos upstream region were noted and deletion analysis suggested that these repeats were involved in the regulation of the level of downstream gene expression.

When the sequence of the ocs gene was published (H. DeGreve et al. (1982) supra), a TATA box-like sequence at the 5'-side of the gene and a polyadenylation signal at the 3'-side of the gene were noted, but no other sequence of potential regulatory significance was pointed out. It was suggested that perhaps because the ocs promoter is positioned close to the edge of the T-DNA, flanking plant sequences could influence the levels of ocs transcription.

C. Koncz et al. (1983), supra showed that sequence information in the region between −295 and −170 was essential for full expression of ocs, but specific sequences responsible for maximal gene expression were not identified. The upstream region of ocs has recently been reexamined and it was found that there is a regulatory sequence element contained within the region between −292 and −116 that acts to enhance or activate ocs gene expression (J. Ellis et (1987) EMBO J. 6:11; U.S. patent application Ser. No. 011,614). The element, termed a plant upstream activating sequence, is a 16 base pair palindromic sequence (5'-ACGTAAGCGCTTACGT-3') which activates the expression of a downstream gene driven by a plant-expressible promoter. A synthetic oligonucleotide comprising the aforementioned sequence or the appropriate fragment of the ocs upstream region was placed 5' to the maize anaerobically-regulated alcohol dehydrogenase (Adh1) promoter with a bacterial chloramphenicol acetyl transferase (CAT) reporter gene; in both instances anaerobic induction of CAT enzyme activity was obtained in stably transformed tobacco plants. Analogous constructions without the transcriptional activating element did not give detectable expression in tobacco when either CAT or Adh1 served as the reporter gene. The functionality of the ocs gene transcription activating element was also determined using transient expression assays in cultured maize cells. Thus, the ability of the ocs transcription activating element to function in both monocotyledonous and dicotyledonous plants was established (J. Ellis et al. (1987) EMBO J. 6:3203-3208; U.S. patent application Ser. No. 011,614).

The presence of a transcription activating element in the upstream region of another T-DNA gene, the mannopine synthase gene (mas), has been suggested by deletion analysis (V. DiRita and S. Gelvin (1987) Mol. Gen. Genet. 207:233). No specific sequence motifs were linked to transcriptional activation.

The entire T-DNA region of an octopine type Ti plasmid, pTi15955 has been sequenced and the sequence has been analyzed for the location of open reading frames (ORFs), putative eukaryotic promoters, ribosome binding sites, and regions with potential secondary structure which might possess regulatory significance (R. Barker et al. (1983) Plant Mol. Biol. 2:335). Among the octopine T-DNA ORFs identified by sequence analysis is the 780 gene which corresponds to ORF 18 in T-right of Barker et al. This ORF was found to be transcribed in plants and is named for the size of its approximately 780 base transcript. The 780 gene product, which is nonessential for virulence, has not been identified, and its function is unknown (J. Winter et al. (1984) Nucleic Acids Res. 12:239; S. Karcher et al. (1984) Mol. Gen. Genet. 194:159). The upstream region of the 780 gene was noted by Barker et al. to have TATA- and CAAT-homologous regions but no other sequences of any potential functional significance were noted.

The present invention is based on a detailed analysis of the upstream regulatory region of the 780 gene which has in part been described by W. Bruce and W. Gurley (1987) Mol. Cell Biol. 7:59.

SUMMARY OF THE INVENTION

This invention is based on the identification and characterization of a plant transcription activating element in the 5'-untranscribed region of the Agrobacterium octopine-type T-DNA gene known as the 780 gene. The 780 gene transcription activating sequence element functions in plants to activate or enhance expression of plant-expressible genes placed under its regulatory control. The 780 gene transcription activating element is functional, in particular, when positioned 5' (upstream) to the transcription start site of a plant-expressible gene. In general, when positioned upstream of a plant-expressible gene, the 780 gene transcription activating element is capable of activating transcription, provided that a functional "TATA" box is present at an appropriate distance from the transcription start site of the plant-expressible gene.

Functional analysis of the upstream region of the 780 gene by deletion mutagenesis demonstrates that all DNA sequence necessary for full transcriptional activation is contained within the region extending to −476 relative to the start of 780 gene transcription (major transcript). A plant transcription activating element is contained within the 780 upstream DNA sequence extending from about −476 to about −229. Deletion of this sequence results in minimal transcription of the 780 structural gene (ca. 0.5% of wild-type transcription). The majority of transcription activating capability is associated with sequences between about −427 and −271, with a significant functional element located between −427 and −396. The sequences between −476 and −427 and −271 and −229 contribute a smaller, yet significant, amount to full transcription activation. Four direct sequence repeats (a, b, c and d, FIG. 1) are found in the 780 upstream region. Three of these repeats (a, b and c) are clustered between −429 and −401 which indicates that one or more of these repeats contribute to transcription activation function. Examples of functional 780 transcription activators include, among others, those that comprise the nucleotide sequences (as in Table 1) −427 to −271, −427 to −229, −476 to −271, −476 to −229, −476 to −200 and −476 to −112. DNA molecules which effect transcriptional activation of genes, as described herein, and which have at least about 90% sequence homology to the functional 780 gene transcription activating elements of the present invention, are considered to be functionally equivalent thereto.

The plant transcription activating element described herein is useful in the art of plant genetic engineering to activate expression of plant-expressible genes placed under its regulatory control. The plant transcription activating element of the present invention is useful, in particular, as a component of a chimeric plant-expressible gene, which can be introduced into a plant cell or plant tissue where the structural gene is expressed.

It is a principal object of this invention to provide a novel transcription activating element which functions in plant tissue, the 780 gene transcription activating element. This sequence element controls the level of transcription and expression of a plant-expressible gene placed under its regulatory control. DNA fragments comprising the sequence extending from about nucleotide −476 to about −229, as in Table 1, function to activate gene expression in plants. The transcription activating element is functional in either orientation. It is preferably placed upstream of the transcription start site from immediately 5' to the TATA box of the gene promoter (e.g. about −40 in the 780 gene) to about 2000 bp 5' of the transcription start site. Ideally the transcription activating element should be located from immediately 5', up to about 600 bp 5' to the TATA sequence, such that the level of expression of the structural gene is increased by the presence of the transcription activating element. In the wild-type 780 gene the activating element is positioned about 200 bp upstream of the TATA sequence. The level of gene expression can be modulated by controlling the distance between the transcription activating element and the promoter sequences. It is preferred that the transcription activating element be placed upstream of the gene it is to regulate. The positioning of more than one copy of the transcription activation element upstream of a plant-expressible gene can result in additional enhancement of transcription activation in plant tissue. The transcription activating element from the 780 gene of T-DNA is functional when placed 5' to any plant-expressible gene. The transcription activating element of the present invention functions generally in all plants, including both dicotyledonous and monocotyledonous plants.

The present invention provides recombinant DNA molecules which comprise the transcription activating element of the T-DNA 780 gene and a plant-expressible gene which is positioned with respect to the transcription activating element such that expression of the gene is regulated thereby. Other regulatory control sequences, including a promoter including "TATA" box and possibly "CCAAT" box motifs and translation termination signals necessary for expression of a given structural gene in a plant may be required, as is well-known in the art. It is preferred that the 780 transcription activating element should be placed 5' to and up to about 2000 bp upstream of the transcription start site of the gene which is to be placed under its control. The 780 gene transcription activating element is more preferably placed 5' to and up to about 650 bp upstream of the gene transcription start site. Construction of the DNA molecules of the present invention is accomplished by conventional techniques using the transcription activating element described above. It is contemplated that any plant-expressible promoter and any plant-expressible structural gene can be employed in the recombinant molecules of the present invention.

It is a further object of the present invention to provide a method of using the recombinant DNA molecules described herein for expressing a structural gene in a plant under the transcriptional control of the transcription activating element of the 780 gene of T-DNA and a plant-expressible promoter. This is accomplished by introducing the recombinant DNA molecule containing the transcription activating element and the gene under its control into plant tissue or plant cells by any means known to the art. In one embodiment of the present invention the recombinant DNA molecule is introduced into plant tissue by T-DNA mediated transfer.

Other objects of this invention are plants, plant cells, and plant tissue genetically modified by the incorporation of a plant-expressible gene complex consisting of the transcription activating element, appropriate promoter and other regulatory sequences, and a structural gene, as described herein and prepared by the methods described herein. The method of the present invention is generally applicable to the expression of structural genes in both monocotyledonous and dicotyledonous plants.

BRIEF DESCRIPTION OF THE FIGURES

FIG. 1A-K illustrate the construction of plasmid pW9-TD:−476/−112-5'A, by insertion of DNA fragment −476/−112 of the upstream region of the 780 gene into the shuttle vector pW9TD:Δ-37. These figures include a diagram to show the location of the 780 gene upstream region within T-right of pTi15955. The −476/−112 and −476/−200 BamHI/SalI fragments of the 780 gene upstream region contain the 780 gene transcription activator. Fragment −476/−112, appropriately modified with BamHI linkers, is inserted 5' to the attenuated Δ-37 780 test gene in pW9-TD:Δ-37. The fragment can be inserted in either orientation, however only one orientation is shown. The fragment can also be inserted at a position 3' to the test gene as indicated in pW9-TD:Δ-37. The hatched area in both plasmids is the SphI-BamHI fragment of pACYC184 containing chloramphenicol resistance gene (cam$^r$) (A. Chang and S. Cohen (1978) J. Bacteriol. 134:1141–1156). The solid black areas are the 780 reference and test genes. The stippled area is the SphI-BamHI subfragment of BamHI fragment 17a of T-left, which is used for homologous recombination with the Ti-plasmid. The black triangle denotes the TacI deletion in the 780 reference gene leader. The 25 bp SalI-BamHI fragment immediately upstream of the test gene is part of the polylinker of pUC−19. In these figures A=AccI; B=BamHI; H=HindIII; S=SalI and Sp=SphI.

FIG. 2 displays the Relative Transcription Levels (RTLs) of the 780 test gene as a function of position and orientation of the 780 gene transcription activator. The horizontal black arrows represent either the −476/−112 or −476/−200 780 gene fragments, as indicated. The open and black boxes denote the regions of the 780 promoter extending from −112 to −38 and from −37 to +1, respectively. The stippled region represents the 780 gene transcribed and 3'-flanking sequences from +1 to about +926 (including about 150 bp of sequence downstream of the poly (A) addition site). The hatched box represents the ΦX174 HaeIII 603 bp fragment with 10 bp SalI linkers added, which is employed to vary the spacing between the activator and the TATA region. RTLs are given for each structural combination as percentages relative to the 780 gene wild type (WT) activity.

DETAILED DESCRIPTION OF THE INVENTION

The following definitions are provided, in order to remove ambiguities to the intent or scope of their usage in the specification and claims.

A recombinant DNA molecule is one which has been either naturally or artificially produced from parts derived from heterologous sources, which parts may be naturally occurring or chemically synthesized molecules, and wherein those parts have been joined by ligation or other means known to the art.

Expression refers to the transcription and translation of a structural gene so that a protein is made. Gene expression can be assessed by direct detection of protein product, by protein gel-electrophoresis or immunological methods, for example. Oftentimes, expression is assessed by detection of the mRNA products of transcription. This method is particularly appropriate for the assessment of transcriptional control factors, such as transcriptional activating elements, since the effects of non-transcriptional factors, such as protein degradation are excluded.

The term plant transcription activating element refers, herein, to functional DNA sequence identified within the 5'-untranscribed region of the 780 gene of the T-DNA of pTi15955. This sequence of DNA can, in an orientation-independent fashion, activate and enhance transcription of genes in plant cells or tissue. The transcription activating element, described herein, functions when positioned 5' to plant-expressible genes. The functionality of DNA fragments containing the transcription activating element of the 780 gene have been assessed by their ability to activate expression of a truncated 780 gene, specifically that which is truncated to position −37. DNA fragments that are functionally equivalent to the 780 gene activating element may be identified using similar assays. A 780 gene transcription activating element can be isolated from the naturally occurring DNA, such as the T-DNA of an octopine plasmid or can be artificially prepared, for example, by the combination of naturally occurring DNA segments or by chemical synthesis of the functional DNA sequence. As is known in the art, the function of a particular DNA molecule is often correlated with its structure, that is, its sequence. In some cases, minor sequence variations have little or no effect on functionality. For purposes of the present work, DNA molecules and fragments having at least about 90% DNA homology to the 780 gene activator containing fragments of the present invention are defined as functionally equivalent thereto.

Promoter refers to sequences at the 5'-end of a structural gene which direct the initiation of transcription. Promoter sequences are necessary, but not always sufficient, to drive expression of the downstream structural genes. The promoter itself may be a composite of segments derived from more than one source, naturally occurring or synthetic. Eukaryotic promoters are commonly recognized by the presence of DNA sequences homologous to the canonical form 5'-TATAA-3' ("TATA" box) about 20–35 bp 5' to the location of the 5'-end of the mRNA (cap site, +1). About 30 bp 5' to the "TATA" box another promoter component sequence is often, but not always, found which is recognized by the presence of DNA sequences homologous to the canonical form 5'-CCAAT-3'. For the purposes of the present description, a promoter is defined to include DNA sequence extending up to about −150 bp 5' (−150) to the transcription initiation site. Any ancillary sequences which may be located 5' to −150 and which may contain functionality including, but not limited to, that of transcription activating element or sequences exerting regulation in response to environmental stimuli, are considered to be promoter-associated elements. For consistency herein, the position of the 780 gene transcription activating element has been given relative to the 780 gene major transcript start site. It should be noted that a promoter is located in relation to the particular transcript whose transcription it initiates. The 780 gene appears to contain two overlapping promoters, one each for the major and minor transcripts.

A plant-expressible gene refers to the combination of a structural gene and the regulatory DNA sequences necessary to allow expression of that structural gene in a plant cell or tissue. A plant-expressible gene may be composed of a structural gene and its homologous regulatory sequences including a promoter or be a chimeric construction composed of regulatory sequence and a structural gene coding sequence from different gene sources. The term structural gene refers to that portion of a gene comprising a DNA segment coding for a protein, polypeptide or portion thereof, possibly including a ribosome binding site and/or a translational start codon. The term can also refer to copies of a structural gene naturally found within the cell, but artificially introduced. In this case, the structural gene naturally occurring in a cell may be reintroduced into a cell as part of a chimeric gene having non-natural regulatory control sequences, for example under the control of a 780 gene transcription activating element. The structural gene may encode a protein not normally found in the plant cell in which the gene is introduced, in which case it is termed a foreign structural gene. A foreign structural gene may be derived in whole or part from a bacterial genome or episome, eukaryotic nuclear or plastid DNA, cDNA, viral DNA, or chemically synthesized DNA. It is further contemplated that a structural gene may contain one or more modifications in either the coding segments or in the untranslated regions which could affect the biological activity or the chemical structure of the expression product, the rate of expression or the manner of expression control. Such modifications include, but are not limited to, mutations, insertions, deletions, and substitutions of one or more nucleotides. The structural gene may constitute an uninterrupted coding sequence or it may include one or more introns, bounded by the appropriate plant functional splice junctions. The structural gene may be a composite of segments derived from a plurality of sources, naturally occurring or synthetic. The structural gene may also produce a fusion protein. For purposes of the present work, a structural gene is considered to include a polyadenylation signal downstream from the translation termination codon. The polyadenylation signal sequence may be that of the structural gene employed or obtained from another source, including for example a chemically synthesized DNA sequence. The polyadenylation signal effects mRNA processing, usually by the addition of polyadenylic acid tracts to the 3'-ends of the precursor mRNAs. It is known that a canonical polyadenylation signal may cause a cleavage of the transcript and not polyadenylation per se (C. Montell et al. (1983) Nature 305:600). It is contemplated that the introduction into plant tissue of recombinant DNA molecules containing the transcription activating element/promoter/structural gene/polyadenylation signal plant expression complex will include constructions wherein any or all of the component parts are not derived from the same gene source.

Plant tissue includes differentiated and undifferentiated tissues of plants including, but not limited to, roots, shoots, leaves, pollen, seeds, tumor tissue, such as crown galls, and various forms of aggregations of plant cells in culture, such as embryos and calli. The plant tissue may be in olanta or in organ, tissue, or cell culture.

The term chemically synthesized, as related to a sequence of DNA, means that the component nucleotides were assembled in vitro using nonenzymatic means. Manual chemical synthesis of DNA may be accomplished using well established procedures (e.g. M. Caruthers (1983) in *Methodology of DNA and RNA Sequencing*, Weissman (ed.), Praeger Publishers (New York) Chapter 1), or automated synthesis can be performed using one of a number of commercially available machines.

Regulatory control refers to the modulation of gene expression by sequence elements positioned appropriately with respect to the transcription initiation site of the gene. This term refers to the positioning of promoter regions and other regulatory sequences, i.e. those responding to stimuli, most often, upstream of the genes which they regulate. Certain regulatory sequences, such as enhancers, can function when placed 3' or 5' to a gene as long as they are proximal to the gene, i.e. within about 1–2 kb of the gene. Regulation may result in an on/off switch for transcription, or it may result in variations in the levels of gene expression. To place a gene under regulatory control of sequence elements means to place it sufficiently close to such sequence elements, and in a position relative to such sequence elements so that the gene is switched on or off, or its level of expression is measurably varied, as is understood by those skilled in the art. In this invention, the transcription activator sequences function when placed 5' to and within about 2000 bp of the transcription start site and upstream therefrom.

Homology as used herein refers to identity of nucleotide sequences. The extent of homology between DNA sequences can be ascertained by direct sequencing or can be empirically determined in DNA hybridization experiments, such as those described in B. D. Hames and S. J. Higgins (1985) *Nucleic Acid Hybridization*, IRL Press, Oxford UK.

The 780 gene of T-DNA comprises about 500 bp of 5'-untranscribed flanking sequence including the promoter and transcription activating element, an open reading frame of about 414 base pairs, and about 150 bp of 3'-flanking sequence which includes the polyadenylation signal. The 780 gene corresponds to open reading frame 18 of the T-DNA of pTi15955, extending from the ATG at position 16,698 to the TAA translation termination codon at position 17,111, as delineated by R. Barker et al. (1983), Plant Mol. Biol. 2:335. The gene is so named because it determines a transcript of about 780 bases in length (S. Karcher et al. (1984) Mol. Gen. Genet. 194:159; J. Winter et al. (1984) Nucleic Acids Res. 12:2391). This gene is carried within the T-right region of the T-DNA of certain octopine-type Ti plasmids, including but not limited to pTi15955 and pTiAch5. The 780 gene product is not necessary for virulence and the function of the 780 gene product remains unknown.

The functionality of DNA sequences in the upstream region of the 780 gene was analyzed by determining the effect of a series of 5' and internal deletion mutations on transcriptional activity in sunflower tumors. Quantitation of the relative activities of these mutants was achieved by incorporation of a homologous reference 780 gene in the same transfer vector with the mutated test gene to serve as an internal standard. A small portion of the leader sequence of the reference 780 gene was deleted in order that RNA derived from the coding sequence of the reference gene could be distinguished from that of the test gene using S1 nuclease hybrid protection mapping. Both the test and reference 780 genes are transferred to plant tissue where relative transcription activities are measured.

S1 mapping experiments employing the wild-type 780 gene coding sequence indicated the presence of a major and a minor transcription start site, as indicated in Table 1, each having "TATA" and "CCAAT" elements. The effect of upstream mutations on transcription of both the major and minor 780 transcripts were assessed, Table 2. Since the mutations examined generally affected expression of both transcripts in a similar way, the analysis of the upstream activating sequence is discussed, herein, in terms of the major transcript and upstream sequences have been numbered in relation to the major transcription start.

Analysis of the transcriptional activity of the 5'-deletion mutants identified the 5'-boundary of the promoter and the promoter-associated elements, and indicated that upstream sequence information was required for efficient expression of the 780 gene. The results of the S1 nuclease hybrid protection mapping demonstrated that relative transcriptional activity decreased as the extent of the 5' -deletions increased (Table 2). This analysis indicated that the 5'-border of the 780 gene lay between −476 and −427 (ca. 8% drop), with a discrete subcomponent of functional importance positioned near this border. The presence of an upstream transcription activating element was revealed by the dramatic reduction in the relative transcription level that resulted when the 31 bp between −427 and −396 was deleted (ca. 50% reduction in promoter activity). It was also evident that other components of the activator were located between −396 and −271; deletion to −271 reduced the relative transcription level to about 6% of the wild type level. Regions −476 to −428 and −271 to −229 contribute a smaller, yet significant amount to transcriptional activation. When only the core promoter (the "TATA" box region at about −30 and TATA- proximal elements) was present, transcription was only 0.5% to 1% of the activity seen with the full activator fragment.

The effect of internal deletions on transcription was also determined (Table 2). Thirteen deletion mutations and one 18-bp duplication mutant were assayed. Two internal deletions, ID-348/−290 and ID-320/−290, are localized within the activator element, as defined by 5'-deletions. Consistent with this, the transcriptional activity of these mutants is 52 and 65%, respectively, similar to the 52% activity of the Δ-368 5'-deletion mutant. The decrease in transcriptional activity observed with internal deletions, ID-252/−171 and ID-249/−98, is consistent with the positioning of the tranpscription activator as determined by 5'-deletions.

Internal deletions, ID-153/−37, ID-112/−37 and ID-76/−37, removing sequence from the intermediate upstream region, either were stimulatory to or had no effect on transcriptional activity. These results suggest that the specific sequence between −153 and −37 is not essential for transcription of the major transcript of 780 gene. The "TATA" and "CCAAT" sequences of the minor transcript are, however, removed in these internal deletions. The specific sequence between −76/−37 appears not to be essential for transcription of either transcript. Two small internal deletions, ID-76/−74 and ID-112/−98, caused significant reduction in transcriptional activity, even though removal of a larger region encompassing these smaller deletions resulted in enhanced transcription (ID-112/−37). Internal deletion mutations not only remove sequence, but also change the spacing between any upstream elements and the "TATA" box or transcription start site, therefore the transcriptional activity observed with internal deletion mutants can result from a combination of factors. It appears that small-scale disruptions in the intermediate upstream region are more deleterious to transcription than the complete removal of this region when accompanied by a decrease in the spacing between the "TATA" and the activator element.

Internal deletions, ID-76/−12 and ID-112/−12 result in almost complete loss of transcription activity of the major transcript (<0.5 and 0.1% activity). These deletion remove the "TATA" sequence of the major transcript.

Thus it appears that the region of DNA sequence encompassing the CAAT-homologous region is not essential for efficient transcription of the 780 gene, while the region encompassing the "TATA" box and proximal sequence is required for transcription to occur.

The results of experiments with deletion mutants suggest that there are at least three components of the upstream activating element of the 780 5'-flanking region: the activator, an intermediate upstream region and the "TATA" region. The most distal component is termed a transcription activating element because of its functional and positional characteristics. Most of the transcription activating activity was associated with DNA sequences between about −427 and about −271, with significant activity associated with sequence extending upstream to −476 and downstream to −229. The intermediate upstream region is located between about −229 and the "TATA" region, about −37. The "TATA" region comprises the TATA-homologous sequence and the sequences proximal to the start of transcription.

The data from internal deletion experiments, also, indicate that there is flexibility in the spacing of the transcription activator relative to the "TATA" region. For example, certain internal deletions (i.e., ID-153/−37, ID-112/−37 and ID-76/−37) which move the activator region 31 to 108 bp closer to the "TATA"

region, enhance or have little effect on transcription activation.

The sequence of the upstream region of the 780 gene is provided in Table 1. In addition to the TATA and CCAAT motifs, no other sequences in the upstream region of the 780 gene have been identified which show strong homology with consensus sequences commonly found in eukaryotic genes (Myers et al. (1986) Science 232:613-618). Furthermore, no significant homologies have been identified between the 780 gene upstream region and sequences in the ocs and nos gene upstream regions that have been associated with activation or enhancement of transcription.

There are, however, four direct repeats positioned throughout the 5'-flanking region (labelled a–d in Table 1). Three of these repeats are clustered near the 5'-end of the activator. Deletion of these sequences, from positions −427 to −396, resulted in a sharp drop in transcriptional activity indicating that the sequence repeats are critical to activator function. Two copies of each repeat a, repeat b and repeat c are found in the region extending from −476 to −220. A third copy of repeat c is found at the 3'-border of the activator. One copy of repeat d is found within the activator region and a second is found within the intermediate upstream region. Repeat c has also been found to occur in the upstream regions of 7 of the 13 known genes of octopine-type DNA and sequences similar to repeat c have been noted in the 5'-flanking regions of nopaline-type T-DNA genes. Such repeats may represent sites of protein-DNA interaction which function in the regulation of gene expression.

Figure 1A:
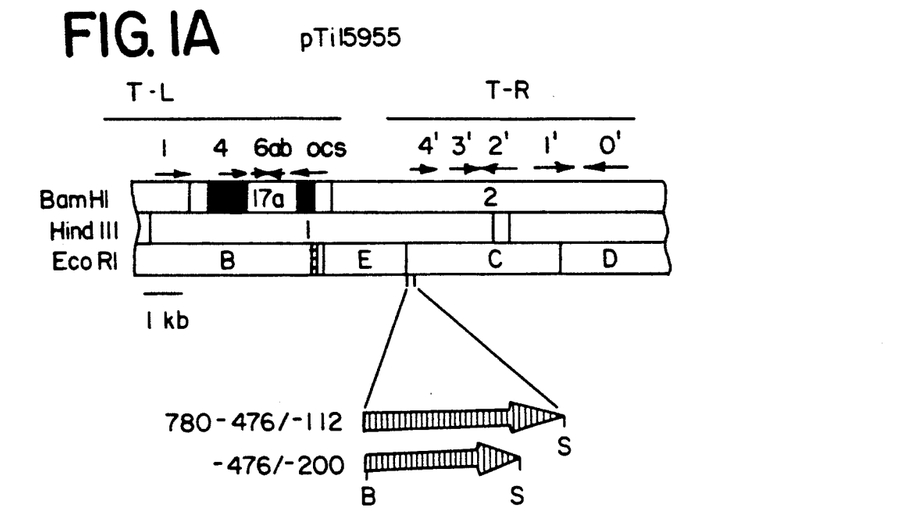
Figure 1B:
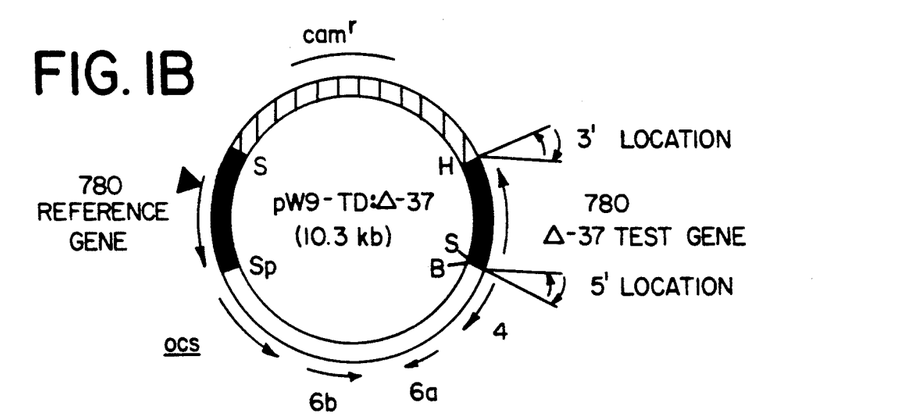
Figure 1C:
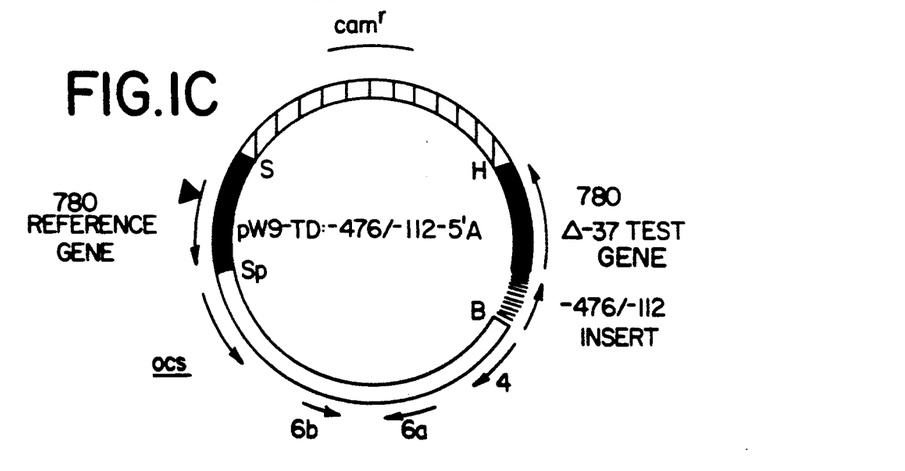

In order to determine the orientational and positional properties of the 780 gene activator element, a restriction enzyme fragment of the 780 gene upstream region containing the activator, extending from −476 to −112 (Table 1) was isolated and inserted into the shuttle vector (pW9-TD:Δ-37), FIG. 1. The effect of positioning this fragment, in both orientations as well as upstream and downstream of a deletion mutant of the 780 gene on transcriptional activity was assessed, FIG. 2. The 780 gene deletion mutant, Δ-37, contained the entire 780 gene coding region but the 5'-flanking sequence was deleted to −37. This mutant, Δ-37, retains the "TATA" region of the major transcript, which is expressed only to about 2% the level of the wild-type 780 gene. Results similar to those obtained with the −476/−112 fragment were obtained with a somewhat smaller, activator-containing fragment, extending from −476 to −200.

Figure 2:
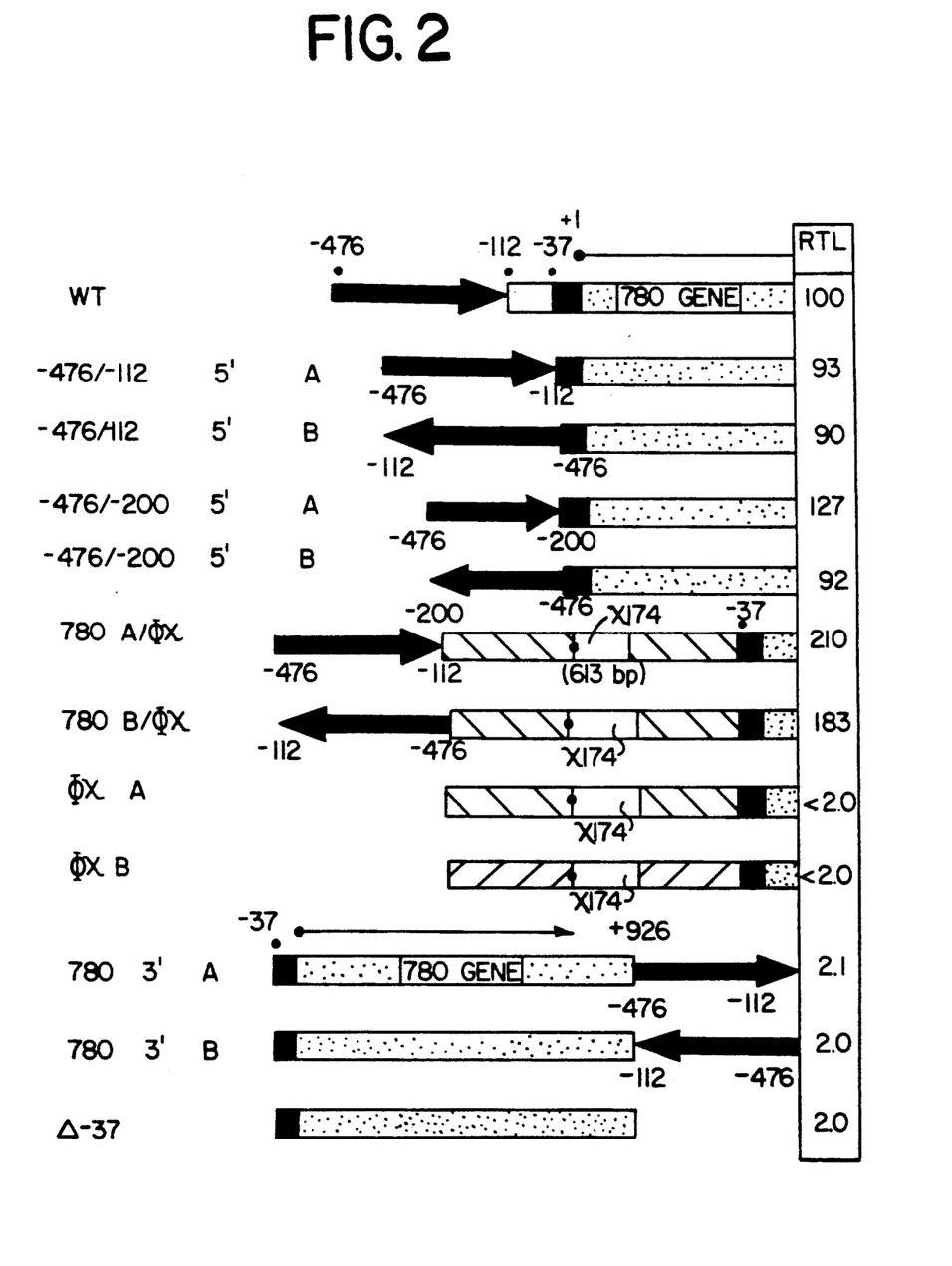

As shown in FIG. 2, it was found that the 780 activator stimulated transcription in a bidirectional manner over relatively large distances 5' from the gene, up to at least about 650 bp from the transcription start site. The distance between the activator and the "TATA" region was varied by insertion of fragments of ΦX174 DNA. The 780 gene transcription activating element will function when positioned up to about 2 kb from the transcription start site.

In the particular construct tested, the 780 activator did not stimulate transcription when positioned 3' to the attenuated Δ-37 780 gene, with intermediate upstream region including a "CCAAT" homologous region removed. This result may be due to the truncation of the 780 gene promoter region rather than to the lack of activator function when positioned 3' to a gene. The 780 activator may enhance transcription when positioned 3' to a less severely attenuated promoter.

The production of genetically modified plant tissue containing and expressing a structural gene under the transcriptional control of a plant transcription activating element and promoter sequences combines the specific teachings of the present disclosure with a variety of techniques and expedients known in the art. In most instances, alternative expedients exist for each stage of the overall process. The choice of expedients depends on variables such as the choice of the vector system for the introduction and stable maintenance of the expression complex, the plant species to be modified and the desired regeneration strategy, and the particular structural gene to be used, all of which present alternative process steps which those of ordinary skill are able to select and use to achieve a desired result. For instance, although the ultimate starting point for obtaining the plant upstream activator is exemplified in the present application by pTi15955, homologous DNA sequences of other octopine-type Ti plasmids, or from different sources, can be substituted as long as the appropriate modifications are made to the procedures for manipulating the DNA carrying the transcription activating element. Similarly, the 780 structural gene can be replaced by a plant-expressible structural gene from another source, again with appropriate procedural modifications. Homologs of structural genes or of other sequences may be identified by the ability of their nucleic acids to cross-hybridize under conditions of appropriate stringency as is well understood in the art. It will be understood that there may be minor sequence variations within sequences utilized or disclosed in the present application. It is well known in the art that some DNA sequences within a larger stretch of sequence are more important than others in determining functionality. A skilled artisan can test allowable variations in sequence, without expense of undue experimentation, by well-known mutagenic techniques which include, but are not limited to, those discussed by D. Shortle et (1981) Ann. Rev. Genet. 15:265; M. Smith (1985) ibid. 19:423; D. Botstein and D. Shortle (1985) Science 229:1193; by linker scanning mutagenesis (S. McKnight and R. Kingsbury (1982) Science 217:316), or by saturation mutagenesis (R. Myers et al. (1986) Science 232:613). These variations may be determined by standard techniques in combination with assay methods described herein to enable those in the art to manipulate and bring into utility the functional units of upstream transcription activating sequence, promoter elements, structural genes, and polyadenylation signals. Using the methods described herein the skilled artisan can without application of undue experimentation test altered sequences within the upstream activator for retention of function. All such shortened or altered functional sequences of the activating element sequences described herein are deemed "780 gene transcription activating elements" and are within the scope of this invention. The final steps of the preferred embodiment for obtaining genetically modified plant tissue include inserting the expression complex into a T-DNA-containing vector, and transferring the recombinant DNA to plant tissue wherein the modified T-DNA becomes stably integrated as part of the genome.

A principal feature of the present invention in its preferred embodiment is the recombinant plasmid having a structural gene whose transcriptional expression is enhanced by the action of the plant transcription activating element from the 780 gene and promoter sequences. These components must be inserted in correct position and orientation relative to one another. It has been determined that the transcription activating element is best placed 5' to the promoter, and that the active sequence should be placed between within about 2000 bp of the gene transcription start site and that the orientation of the transcription activating sequence is not important to functionality. To be controlled by the transcription activating element-promoter complex, the structural gene must be inserted on the 3'-side of said complex. (A few known promoters exert bidirectional control, in which either side of the promoter could be considered downstream.) That portion of the structural gene which ultimately codes for the amino terminus of the protein is the 5'-end (upstream) of the gene, while that end which codes for amino acids near the carboxyl end is termed the 3'-end (downstream) of the gene. The 5' to 3' polarity designation established by the orientation of the coding region is extended to cover flanking sequences including the promoter. The 5'-end must be adjacent to the 3'-end of the transcription activator-promoter complex. The polyadenylation signal must be located in the correct orientation downstream from the 3'-end of the coding sequence. Another consideration is the distance between the functional elements of the expression complex. Substantial variation appears to exist with regard to these distances; therefore, the distance requirements are best described in terms of functionality. As a first approximation, reasonable operability can be obtained when the distances between functional elements are similar to those in the genes from which they were derived. It is contemplated that one might vary the distances between the transcription activating element and other functional sequences, and thus achieve variations in the levels of expression of the structural gene. In the case of constructions yielding fusion proteins an additional requirement is that the ligation of the two genes or fragments thereof must be such that the two coding sequences are in the same reading frame, a requirement well understood in the art. An exception to this requirement exists in the case where an intron separates the coding sequence derived from one gene from the coding sequence of the other. In that case, the coding sequences must be bounded by compatible splice sites, and the intron splice sites must be positioned so that the correct reading frame for both genes is established in the fusion after the introns are removed by post-transcriptional processing. Differences in rates of expression or developmental control may be observed when a given gene is inserted under the control of different plant upstream transcription activating element-promoter complexes.

The recombinant DNA molecule carrying the desired structural gene under the control of promoter sequences and the 780-derived transcription activator may be introduced into plant tissue by any means known to the art. The technique used for a given plant species or specific type of plant tissue depends on the known successful techniques. Means for introducing recombinant DNA into plant tissue include, but are not limited to transformation (J. Paszkowski et al. (1984) EMBO J. 3:2717), electroporation (M. Fromm et al. (1985) Proc. Natl. Acad. Sci. USA 82:5824), microinjection (A. Crossway et al. (1986) Mol. Gen. Genet. 202:179), or T-DNA mediated transfer from *Agrobacterium tumefaciens* to the plant tissue. There appears to be no fundamental limitation of T-DNA transformation to the natural plant host range of Agrobacterium. Successful T-DNA mediated transformation of monocots (G. M. S. Hooykaas-Van Slogteren et al. (1984) Nature 311:763-764), gymnosperms (A. M. Dandekar et al. (1987) Biotechnol. 5:5897-590) and algae (R. L. Ausich EPO Publication No. 108,580) has been reported. Representative T-DNA vector systems are described in the following references: G. An et al. (1985) EMBO J. 4:277; L. Herrera-Estrella et al. (1983) Nature 303:209; L. Herrera-Estrella et al. (1983) EMBO J. 2:987; L. Herrera-Estrella et al. (1985) in *Plant Genetic Engineering*, New York: Cambridge University Press, p.63. Once introduced into the plant tissue, the expression of the structural gene may be assayed by any means known to the art, and expression may be measured at the transcriptional level or as protein synthesized. Techniques are known for the in vitro culture of plant tissue, and in a number of cases, for regeneration into whole plants. Procedures for transferring the introduced expression complex to commercially useful cultivars are known to those skilled in the art. Plant tissue transformed to contain the DNA molecules of the present invention can be identified by the presence of the DNA fragments introduced, for example, using DNA hybridization assays. The presence of the introduced DNA fragments is an identifiable phenotype of the transformed tissue.

As novel means are developed for the stable insertion of foreign genes into plant cells and tissue and for manipulating transformed cells and tissue to obtain transformed plants, those of ordinary skill in the art will be able to employ the DNA fragments and constructs of the present invention in combination with any such desired novel means without exercise of undue experimentation. In a representative embodiment (pW9-TD:−476/−112-5'A, see FIG. 1), the upstream activator has been inserted into an expression plasmid 5' to the "TATA" element of a promoter and structural gene at a BamHI site. As will be apparent to those of ordinary skill in the art, components of the expression complex may be joined by any naturally occurring or artificially engineered restriction sites convenient for vitro manipulations. The major consideration is that the sequences at the junctions remain compatible with transcriptional and translational functionality.

The following examples are provided for illustrative purposes only and are not intended to limit the scope of the invention. The examples utilize many techniques well known and accessible to those skilled in the arts of molecular biology, in the manipulation of recombinant DNA in plant tissue, and in the culture and regeneration of transformed plants. Enzymes are obtained from commercial sources and are used according to the vendors' recommendations or other variations known in the art. Reagents, buffers and culture conditions are also known to the art. References containing standard molecular biological procedures include T. Maniatis et al. (1982) Molecular Cloning, Cold Spring Harbor Laboratory, Cold Spring Harbor, N.Y.; R. Wu (ed.) (1979) Meth. Enzymol. 68; R. Wu et al. (eds.) (1983) Meth. Enzymol. 100 and 110: L. Grossman and K. Moldave (eds.) (1980) Meth. Enzymol. 65; J. Miller (ed.) (1972) *Experiments in Molecular Genetics*, Cold Spring Harbor Laboratory, Cold Spring Harbor, N.Y.; Old and Primrose (1981) *Principles of Gene Manipulation*, University of California Press, Berkeley, Calif.; R. Schlief and P. Wensink (1982) *Practical Methods in Molecular Biology;* Glover (ed.) (1985) *DNA Cloning*, Vols. I and II, IRL Press, Oxford, UK; Hames and Higgins (eds.) (1985) *Nucleic Acid Hybridization*, IRL Press, Oxford, UK; Setlow and A. Hollaender (1979) *Genetic Engineering: Principles and*

*Methods*, Vols. 1–4, Plenum Press, New York. Abbreviations and nomenclature, where employed, are deemed standard in the field and commonly used in professional journals such as those cited herein.

EXAMPLE 1

This example describes the cloning, transformation, and assay strategies for examining the transcriptional expression of a reporter gene promoter relative to a reference gene.

1.1 Construction of an Intermediate Shuttle Vector Containing the 780 Reference Gene The 780 gene was initially subcloned from plasmid p403 (W. Gurley et al. (1979) Proc. Nat. Acad. Sci. USA 76:2828; N. Murai and J. Kemp (1982) Proc. Nat. Acad. Sci. USA 79:86). The EcoRI-SphI fragment of p403 carried DNA extending from 16,202 to 17,601 bp within T-right of pTi15955 (R. Barker et al. (1983) Plant Mol. Biol. 2:335). The isolated fragment was ligated with EcoRI-SphI-cut pUC-19 (J. Norrander et al. (1983) Gene 26:101). This plasmid, designated pUC-19:780, contained the complete 780 gene consisting of 476 bp of 5'-flanking sequences, the protein coding region, and ca. 200 bp downstream of the poly(A) addition signal.

The *Escherichia coli* host used for recombinant DNA work was strain LE392.

A reference analog of the 780 gene was constructed so that relative transcription levels of test genes could be measured. A derivative of pUC-19:780, in which sequences 5' of −290 in the 780 gene had been deleted, was chosen because TagI sites upstream of -290 would have interfered with the construction of the reference gene. The deleted pUC-19:780 plasmid was digested with TagI and religated with the effect of removing an 8 bp TagI fragment from the DNA determining the leader region of the 780 message. After transformation into *E. coli*, the plasmid structures were confirmed by restriction analysis. The 8 bp deletion in the 5'-untranslated leader sequence permits the discrimination of test and reference gene transcripts by S1 nuclease hybrid protection analysis.

The shuttle vector pW9 was created by inserting a 4.2 kb BamHI-SphI fragment of T-left (pTi15955) from p233G (W. Gurley et al. (1986) Mol. Cell. Biol. 6,559) into pACYC184 (A. Chang and S. Cohen (1978) J. Bacteriol. 134,1141). The p233G-derived fragment includes about 3.8 kb of T-left DNA and about 0.4 kb of pBR322 sequence. The T-left sequences provide the site for the homologous recombination of the shuttle vector into the Ti plasmid of *Agrobacterium tumefaciens* Ag5260, which is described below. The reference 780 gene was subsequently cloned into the shuttle vector pW9 as a 1.2 kbp SalI-SphI fragment to give pW9-TD.

1.2. Generation of Deletions and Duplications in the Upstream Region of the 780 Gene pUC-19:780 (5 µg) was linearized with EcoRI, and 5'-deletions were generated by digesting with exonuclease Bal31 (Bethesda Research Laboratories) (50 U/ml, 0.05 ml volume). SalI linkers were added (T. Maniatis et al. (1982) *Molecular Cloning*, Cold Spring Harbor Laboratory, Cold Spring Harbor, N.Y.). The molecules were then digested with HindIII to liberate the truncated 780 fragments as SalI-HindIII fragments. These fragments were then ligated to pUC-19 which had been cut with SalI and HindIII. The extent of the deletions were determined by sequence analysis as described previously (A. Maxam and W. Gilbert (1980) Meth. Enzymol. 65:499; F. Sanger et al. (1981) J. Mol. Biol. 143:161).

To prepare for producing 3'-deletions extending into the 5'-untranscribed flanking region of the 780 gene, the EcoRI site of pUC-19:780 was first changed to a BamHI site by linker addition (T. Maniatis et al. (1982) *Molecular Cloning*, Cold Spring Harbor Laboratory, Cold Spring Harbor, N.Y.). The modified plasmids were then cut with HincII, and treated with Bal31 as above. The HincII site is at position 17,075 (R. Barker et al. (1983)). SalI linkers were added, as above, and after cutting with SalI and BamHI, the 780-derived fragments were ligated to similarly cut pUC-19. Deletions were determined by sequence analysis as described above.

Internal deletion and duplication mutants were constructed after the joining of appropriate pairs of 5'- and 3'-deletion mutants. The appropriate 5'-deletions were isolated as SalI-HindIII fragments and ligated into SalI-HindIII-cut pUC-19:780 3'-deletion clones.

1.3 Construction of Shuttle Vector Containing a Test Gene

The pUC-19:780 derivatives were cut with BamHI and HindIII, ligated to likewise cut pW9-TD, and transformed into *E. coli*. Restriction analysis confirmed that the 780-derived fragment was inserted into test plasmids.

1.4 Vector Transfer and Tumor Formation

To prevent homologous genetic recombination between the 780 gene of the resident Ti plasmid and 780 derivatives on the incoming shuttle vectors, it was necessary to create a mutant derivative of *A. tumefaciens* (Str) which was named strain Ag5260. The endogenous 780 gene of pTi15955 was removed from T-right to facilitate the analysis of mutated 780 promoters introduced into T-left. The 4.7 kb XhoI-HindIII fragment (15,208 to 19,953 bp as in Barker et al. (1983) Plant Mol. Biol. 2:335) containing the 780 gene was replaced with a 1.5 kb SalI-HindIII fragment from transposon Tn5 (S. Rothstein et al. (1980) Cell 19,795), which confers resistance to 50 µg/ml kanamycin. Substitution of the deleted T-right fragment was achieved by double homologous recombination as described by A. Matzke and M. Chilton (1981) J. Mol. Appl. Genet. 1:39, except that pH1J1 (J. Beringer et al. (1978) Nature 276:633) was used instead of R751-pMG2 to select for recombinants. pH1J1, however, seemed to interfere with the introduction of the shuttle vectors and was therefore removed from Ag5260 by enrichment for ampicillin-sensitive bacteria using a carbenicillin-cycloserine procedure as described by J. Miller (in *Experiments in Molecular Genetics* (1972) Cold Spring Harbor Laboratory, Cold Spring Harbor, N.Y.). The deleted Ti plasmid also lacked the left border sequence of T-right, the gene corresponding to the 1050 transcript, and most of the 3'-terminus of the gene encoding the 1450 transcript (J. Winter et al. (1984) Nucleic Acids Res. 12:2391). Mutant *A. tumefaciens* Ag5260 was used as the recipient for shuttle vectors containing the various constructions containing 780 derivatives or upstream activating sequences. It was from this strain that the recombinant molecules were transferred to plant tissue.

Double gene shuttle vectors were transferred from *E. coli* LE392 into *A. tumefaciens* Ag5260 by triparental conjugation on solid nutrient medium as described by R. Fraley et al. (1983) Proc. Nat. Acad. Sci USA 80:4803. The resulting transconjugant colonies were selected by growth on AB minimal medium (M. Chilton et al. (1974) Proc. Natl. Acad. Sci. USA 71:3672) containing streptomycin (250 μg/ml), kanamycin (20 μg/ml), and chloramphenicol (17 to 20 μg/ml) for 3 to 5 days at 28° C.

Tumors were incited on sunflower (*Helianthus annuus* cv. Large Grey) seedlings, and the plants were grown as previously described (W. Gurley et al. (1986) Mol. Cell Biol , 6:559). After 14 to 16 days of tumor growth, an average of 200 to 300 tumors for each plasmid construction were harvested and immediately frozen with liquid nitrogen.

1.5 Assay of Transcriptional Expression

Transcriptional expression of the test and reference genes were assayed by S1 nuclease hybrid protection. Analyses were performed with approximately 15 μg of poly(A)-enriched RNA isolated from sunflower tumors as previously described (E. Czarnecka et al. (1984), Plant Mol. Biol. 3,45; W. Gurley et al. (1986) supra. The hybridization probe, covering from −74 to +60 bp, was isolated from the 5'-deletion clone p −74 and was 5'-end labelled at the HpaII site located at position +60 bp. This probe (SalI-HpaII fragment) contains the wild-type leader and flanking sequences of the test gene. Poly(A) RNA was hybridized with the double stranded DNA probe overnight at 38° C. After S1 nuclease (50 U/ml) digestion at 23° C. for 30 min, the protected hybrids were fractionated on an 8% polyacrylamide gel containing 7M urea and exposed to XAR-5 (Kodak Co.) film for 1 to 2 days at −70° C.

Relative transcript levels were defined as the ratio of cpm of the test gene transcripts to cpm of the reference gene transcripts divided by the ratio of cpm of wild-type transcripts to cpm of its reference gene transcripts (P. Dierks et al. (1983) Cell 32:695). Radioactive bands were cut out of the gel and used for Cerenkov counting. All the relative transcript levels represent an average of three or more independent hybridization experiments.

The activities of test genes (those with deletions or duplications in the 5'-untranscribed regions) were compared to the activity of a reference 780 gene, in which the −290 to +1 region remained intact. The transcript of the reference gene was 8 bp shorter than transcripts from the test genes, and could be distinguished by S1 nuclease hybrid protection mapping. When the wild-type leader was used as a hybridization probe, the basis of transcript discrimination was due to a local region of nonhomology between the DNA probe and the reference gene transcript, which allowed S1 nuclease cleavage in the resulting 8 bp loop in the labelled DNA. The major start site of transcription of the wild-type gene maps 60 bp upstream of the HpaII site. When the RNA from tumors containing only the reference gene was subjected to S1 hybrid protection analysis, a cluster of bands was seen at the predicted position of 46 to 54 bp. The position of the cluster corresponded to the sizes of fragments resulting from cleavage in the predicted 8 bp loop in the probe-RNA hybrid. When RNA from tumors containing both test and reference genes was analyzed, two clusters of protected hybrids were seen at the predicted positions, confirming that this method could be used to assess the relative activity of these two promoters. The signal resulting from the test gene transcript is a cluster rather than a single band. A weakly protected band at 120 bp was observed. This corresponded to the minor transcript with the start site 60 bp 5' to the major start site, defined as +1. The level of minor transcripts was judged to 1 to 10% of that of major transcripts. The relative transcription levels (RTL) as percentages of wild-type activity of a series of 5'- and internal deletions of the 780 gene upstream region are shown in Table 2. 5'-deletion mutants are labeled using the 3'-end point of the deletion, i.e. (delta)-427 (a 5'-deletion extending to −427). Internal deletions are labelled with both end points of the deletion, i.e. ID-348/−290 (an internal deletion extending from −348 to −290). RTLs of >10 varied by ±10% or less between experiments. RTLs of <10 varied by less than ±4%.

EXAMPLE 2

Characterization of the Transcription Activating Element

2.1. Orientation Dependence of the Transcription Activating Element

The −476 to −112 fragment of DNA (−476/−112 fragment; see FIG. 1) was used for characterization of the properties of the 780-derived transcription activating element. This fragment was removed from the pUC19:780 derivative containing the 3'-deletion extending to −112. The SalI site at the 3'-end of the 780 fragment was converted to a BamHI site by linker addition as described in T. Maniatis et al. (1982). Conversion of the fragment to a BamHI fragment allowed the cloning of the activator in both orientations upstream of the 5'-deletion to −37 in pW9-TD:Δ-37 (FIG. 1). The SalI site of the −476 to −200 780 fragment was also converted to a BamHI site by linker addition. After removal of the adapted fragments as BamHI fragments, each was ligated into pW9-TD:Δ37. After transformation the plasmid profiles were determined by restriction endonuclease analysis and representative plasmids were chosen so that each orientation of each fragment was tested. FIG. 2 diagrams the various test constructs containing the −476/−112 activator and provides RTLs.

The function of the 780 activator element in promoting transcription of the promoter deleted to −37 was assessed by S1 nuclease hybrid protection as described above. The construct wherein the −476 to −112 region is placed upstream of the −37, and wherein there are 25 bp of the pUC19 polylinker intervening, gave nearly wild-type transcription levels (93%). When the −476 to −112 fragment was inserted in the reverse orientation (relative to wild-type) there was 90% of wild-type transcription activity. In the construction wherein the −476 to −200 fragment was inserted in the wild-type orientation and with the 25 bp of the polylinker intervening, there was greater than wild-type transcription (127%). In the reverse orientation, which had the 25 bp of the polylinker distal to the TATA region, there was 92% relative transcription. Therefore, the orientation of the upstream activating element does not significantly affect its ability to increase transcriptional efficiency. Similar results were obtained on assay of RTLs of the −476/−200 activator fragment, except that the A orientation showed somewhat enhanced activity.

2.2. Effect of Increased Distance Between the Activator and the Core Promoter The activator element region contained within the 780 gene fragment extending from −476 to −112 was tested for activity when about 540 bp of spacer DNA intervened between that fragment and the TATA of the truncated 780 gene promoter. A 613 bp HaeIII fragment of ΦX174 was converted to a SalI fragment by the addition of SalI linkers as described above, and was inserted between the 780 upstream region and the core promoter. The construction in which the 780 gene upstream activator was in its wild-type orientation gave approximately twice wild-type transcription levels (210%). The corresponding construction in which the −476 to −112 fragment was in the reversed orientation gave slightly lower relative transcription levels (183%). Control experiments in which only the ΦX174-derived fragment was placed 5' to the 780 core promoter confirmed that piece of DNA had no plant transcription activating capability.

2.3. Activity of the Activator Placed 3' to the Gene

Because the upstream transcription activating element had some properties of an enhancer-like element, it was tested for its ability to activate transcription of the truncated 780 promoter when placed 3' to the gene in pW9-TD:Δ-37. The −476 to −112 fragment was modified by the addition of HindIII linkers and was positioned at the HindIII site 200 bp downstream of the poly(A) addition site, about 1 kbp from the core promoter. Both orientations of the 780 upstream fragment were tested in this position. When positioned 3' to the gene, there was no detectable enhancement of transcription originating from the core promoter.

EXAMPLE 2.4

Analysis of the DNA Sequence of the 780 Transcription Activating Element

The DNA sequence of the −476 to +60 region of the 780 gene was analyzed by computer for regions of dyad symmetry and for reiterated sequences. Table 1 gives this sequence and illustrates the repeated sequence elements. Within the −440 to −200 region there are two copies of the a repeat (TCCTTTCGAC), two copies of the b repeat (CACGGAT), and three copies of the c repeat (TTGAAAA). There is one copy of the d repeat (CTTTAGG) within this region and a second in the region between −200 and −112.

TABLE 1

DNA Sequence of the Upstream Region of the T-DNA 780 Gene[a,b]

```
                     −470                                                          −430
AGAATTCGTGCCAATCCATTTTGTTTTGATTGTCTTGTAAAGTTTTTCC

−380
TTTCGACCCGCTAATCACGGATTGAAAAATCAACGCTTCACTCCTTTCGA
     a                  b    c                           a

−330
CTTTTTTAAAGCCGTTTCTAAAATGAAATTCTAATCTTTGAAAATGGAAA
                                                 c

−280
TTTATGCTATATGACTTTATCGCCGTGAATAATTAAAGGAGATTCAGACG

−230
GAACTTTAGGCGCTCATTTCGCGACTGGCCCACGGATGATGTAAAACACT
     d                                       b

−180
ACCTAACAAATTTGAAAAAGACGCCAACCACCGATATAGCCGGTCCAAAG
              c

−130
TCGCATCCACTGAAGTACTCATGATCTTTTGAAGGGTAAAAATGTGCTTT
                                                              d

−80
AGGTCCACTAATTCCCCTGTTGAGTAGGTAACGCCTCAATATATGGAAAT
                                                 minor "TATA"

−30
TGCCTCCGAATTTCTCAATTCAATCTTTTGGCATTGTGAGCGGACTCCTA
                                  minor start site +1                                 +20
TAAATATTAGAACCTCTGCCCTTGCACTCGCCATCGAAACATCGAGCAAT
major "TATA"                    major start site

+60
GAGTTATTATTGGATAGATTAAGGCGCAAGCCCGCCGGAA
```

[a]Nucleotide sequence is listed from 5' to 3' and numbered from the major transcription start site.
[b]Direct repeat sequences a, b, c and d are underlined and labelled.

TABLE 2

Relative Transcription Activity of 780 Gene Deletion Mutants[a]

| Deletion Mutant | RTL Major | RTL Minor |
|---|---|---|
| Wild-type | 100 | 100 |
| Δ-427 | 92 | 68 |
| Δ-396 | 55 | 39 |
| Δ-368 | 52 | 35 |
| Δ-336 | 35 | 30 |
| Δ-311 | 30 | 33 |
| Δ-290 | 21 | 20 |
| Δ-271 | 6 | 7 |
| Δ-229 | 1 | 3 |
| Δ-171 | 0.5 | 2 |
| Δ-97 | 0.5 | 1 |
| Δ-74 | 0.5 | 2 |
| +32 | 0.5 | 1 |
| ID-348/-290 | 52 | 36 |
| ID-320/-290 | 65 | 60 |
| ID-153/-37 | 106 | 0.1 |
| ID-112/-37 | 143 | 0.1 |
| ID-76/-37 | 90 | 64 |
| ID-252/-171 | 28 | 30 |
| ID-249/-98 | 17 | 32 |
| ID-153/-171[b] | 36 | 33 |
| ID-153/-98 | 70 | 123 |
| ID-112/-98 | 42 | 96 |
| ID-112/-74 | 47 | 24 |
| ID-76/-74 | 38 | 49 |
| ID-112/-12 | 0.5 | 0.1 |
| ID-76/-12 | 0.1 | 43 |

[a]RTLs are given as percentages of wild-type activity for the major and minor promoters. RTLs of >10 varied by ±10% or less between experiments. RTLs of <10 varied by ±4% or less between experiments.
[b]This mutant contains a duplication of upstream sequence between −153 and −171.

We claim:

1. A recombinant DNA molecule comprising a T-DNA 780 gene transcription activating element which comprises a nucleotide sequence as in Table 1, from about nucleotide −427 to about nucleotide −348 or a functionally equivalent nucleotide sequence with at least about 90% homology thereto and which further comprises a nucleotide sequence from about nucleotide −290 to about nucleotide −271 or a functionally equivalent nucleotide sequence, with at least about 90% homology thereto, and a plant-expressible gene comprising a TATA region wherein said gene is not the 780 gene and wherein said gene is expressed at an enhanced level under the regulatory control of said transcription activating element.

2. The recombinant DNA molecule of claim 1 wherein said 780 gene transcription activating element comprises the nucleotide sequence as in Table 1, from about nucleotide −476 to about nucleotide −229 or a functionally equivalent nucleotide sequence being at least about 90% homologous thereto.

3. The recombinant DNA molecule of claim 1 wherein said 780 gene transcription activating element comprises the nucleotide sequence as in Table 1, from about nucleotide −476 to about nucleotide −200 or a functionally equivalent nucleotide sequence being at least about 90% homologous thereto.

4. The recombinant DNA molecule of claim 1 wherein said 780 gene transcription activating element comprises the nucleotide sequence as in Table 1, from about nucleotide −427 to about nucleotide −229 or a functionally equivalent nucleotide sequence being at least about 90% homologous thereto.

5. The recombinant DNA molecule of claim 1 wherein said 780 gene transcription activating element comprises the nucleotide sequence as in Table 1, from about nucleotide −476 to about −112 or a functionally equivalent nucleotide sequence being at least about 90% homologous thereto.

6. The recombinant DNA molecule of claim 1 wherein said transcription activating element is positioned 5' to and up to about 2000 bp upstream of a transcription start of said plant-expressible gene.

7. The recombinant DNA molecule of claim 6 wherein said transcription activating element is positioned 5' to and up to about 650 bp upstream from the transcription start of said plant-expressible gene.

8. The recombinant DNA molecule of claim 1 wherein said transcription activating element is positioned 5' to the transcription start of said plant-expressible gene and immediately 5' to a 5'-end of a "TATA" region of said plant-expressible gene.

9. The recombinant DNA molecule of claim 1 wherein said plant-expressible gene is a chimeric gene.

10. The recombinant DNA molecule of claim 9 wherein said chimeric plant-expressible gene comprises a T-DNA promoter region.

11. A method for activating the expression of a plant-expressible gene in plant tissue, said method comprising the steps of:
(a) inserting a T-DNA 780 gene transcription activating element which comprises a nucleotide sequence, as in Table 1, from about −427 to about nucleotide −348 or a functionally equivalent sequence with at least about 90% homology thereto and further comprises a nucleotide sequence from about nucleotide −290 to about −271 or a functionally equivalent nucleotide sequence being at least about 90% homologous thereto into a recombinant DNA molecule which comprises said plant-expressible gene, wherein said plant-expressible gene is not the 780 gene and wherein said gene comprises a TATA region, in such a way that said transcription activating element increases the expression of said plant-expressible gene, and
(b) introducing said recombinant DNA molecule containing said transcription activating element into plant tissue such that said plant-expressible gene is expressed under the control of said transcription activating sequence in said plant tissue.

12. The method of claim 11 wherein said transcription activating element is inserted 5' to said plant-expressible gene.

13. The method of claim 11 wherein said transcription activating element is inserted into said DNA molecule 5' to said plant-expressible gene and up to about 2000 bp upstream of the transcription start site of said plant-expressible gene.

14. The method of claim 11 wherein said transcription activating element is positioned 5' to and up to about 650 bp upstream from the transcription start of said plant-expressible gene.

15. The method of claim 11 wherein said transcription activating element is positioned 5' to a transcription start of said plant-expressible gene and immediately 5' to the 5'-end of a "TATA" region of said plant-expressible gene.

16. The method of claim 11 wherein said 780 gene transcription activating element comprises a nucleotide sequence as in Table 1, from about nucleotide −476 to about nucleotide −229 or a functionally equivalent nucleotide sequence at least about 90% homologous thereto.

17. The method of claim 11 wherein said 780 gene transcription activating element comprises a nucleotide sequence as in Table 1, from about nucleotide −476 to about nucleotide −200 or a functionally equivalent nucleotide sequence at least about 90% homologous thereto.

18. The method of claim 11 wherein said 780 gene transcription activating element comprises a nucleotide sequence as in Table 1, from about nucleotide −427 to about nucleotide −229 or a functionally equivalent nucleotide sequence at least about 90% homologous thereto.

19. The method of claim 11 wherein said 780 gene transcription activating element comprises a nucleotide sequence as in Table 1, from about nucleotide −476 to about nucleotide −112 or a functionally equivalent nucleotide sequence at least about 90% homologous thereto.

20. The method of claim 11 wherein said transcription activating element activates expression of an attenuated 780 promoter and comprises one or more copies of the repeat sequence a: 5'-TCCTTTCGAC-3'.

21. The method of claim 11 wherein said transcription activating element activates expression of an attenuated 780 promoter and comprises one or more copies of the repeat sequence b: 5'-CACGGAT-3'.

22. The method of claim 11 wherein said transcription activating element activates expression of an attenuated 780 promoter and comprises one or more copies of the repeat sequence c: 5'-TTGAAAA-3'.

23. The method of claim 11 wherein said transcription activating element activates expression of an attenuated 780 promoter and comprises one or more copies of the repeat sequence d: 5'-CTTTAGG-3'.

24. The method of claim 11 wherein said plant tissue is from a dicotyledonous plant.

25. The method of claim 11 wherein said plant tissue is sunflower tissue.

26. The method of claim 11 wherein said plant tissue is from a monocotyledonous plant.

27. The method of claim 11 wherein said recombinant DNA molecule is introduced into plant tissue by T-DNA mediated transfer.

28. The recombinant DNA molecule of claim 1, wherein said 780 gene transcription activating element comprises a nucleotide sequence selected from the group of nucleotide sequences from the upstream region of the 780 gene consisting of from about nucleotide −427 to about nucleotide −271, from about nucleotide −476 to about nucleotide −229, from about nucleotide −476 to about nucleotide −200, from about nucleotide −427 to about nucleotide −229, and from about nucleotide −476 to about nucleotide −112, as in Table 1.

29. An isolated DNA fragment consisting essentially of a T-DNA 780 gene transcription activating element, which element comprises the nucleotide sequence from about nucleotide −427 to about nucleotide −348 and which element further comprises the nucleotide sequence from about nucleotide −290 to about nucleotide −271, as in Table 1.

30. An isolated DNA fragment consisting essentially of a T-DNA 780 gene transcription activating element, which element is the nucleotide sequence from about nucleotide −476 to about nucleotide −229, as in Table 1.

31. An isolated DNA fragment consisting essentially of a T-DNA 780 gene transcription activating element, which element is the nucleotide sequence from about nucleotide −476 to about nucleotide −200, as in Table 1.

32. An isolated DNA fragment consisting essentially of a T-DNA 780 gene transcription activating element, which element is the nucleotide sequence from about nucleotide −427 to about nucleotide −229, as in Table 1.

33. An isolated DNA fragment consisting essentially of a T-DNA 780 gene transcription activating element, which element is the nucleotide sequence from about nucleotide −476 to about nucleotide −112, as in Table 1.

34. A method for activating the expression of a plant expressible gene in plant tissue, said method comprising the steps of:
(a) inserting a T-DNA 780 gene transcription activating element which comprises a nucleotide sequence, as defined in Table 1 from about nucleotide −427 to about nucleotide −271, into a recombinant DNA molecule which comprises the plant-expressible gene, wherein said plant-expressible gene is not the 780 gene, and wherein said plant-expressible gene comprises a TATA region, in such a way that said transcription activating element increases the expression of said plant-expressible gene, and
(b) introducing said recombinant DNA molecule containing said transcription activating element into plant tissue such that said plant-expressible gene is expressed under the control of said transcription activating element in said plant tissue.

* * * * *